US005332658A

United States Patent [19]

Dyall-Smith et al.

[11] Patent Number: 5,332,658

[45] Date of Patent: Jul. 26, 1994

[54] RECOMBINANT HUMAN ROTAVIRUS VP7 SEROTYPE 4

[75] Inventors: Michael L. Dyall-Smith, Kew; Chris Hum, Boronia; Ian H. Holmes, Canterbury; Michael A. Johnson, North Ryde; Peter R. Reeves, Glebe, all of Australia

[73] Assignee: The University of Melbourne, Victoria, Australia

[21] Appl. No.: 899,216

[22] Filed: Jun. 16, 1992

Related U.S. Application Data

[63] Continuation of Ser. No. 473,959, filed as PCT/AU88/00298, Aug. 10, 1988, abandoned.

[30] Foreign Application Priority Data

Aug. 10, 1987 [AU] Australia ........................ PI3643

[51] Int. Cl.[5] ........................ C12Q 1/68; C12Q 1/70; C12N 15/33; C12N 15/63; A61K 39/12

[52] U.S. Cl. ........................ 435/5; 435/6; 435/320; 435/252.3; 435/243; 435/240.1; 435/252.33; 424/186.1; 424/215.1; 424/192.1; 536/23.72; 536/24.32

[58] Field of Search ................ 435/6, 69.1, 69.3, 69.9, 435/71.1, 320.1, 243.1, 240.1, 5; 935/9, 11, 12, 24, 27, 31, 66, 78; 536/2-7, 23.72, 24.32; 424/92

[56] References Cited

U.S. PATENT DOCUMENTS 4,853,333 8/1989 Hsiao et al. .

5,186,933 2/1993 Estes ........................ 424/89

FOREIGN PATENT DOCUMENTS 8505122 11/1985 PCT Int'l Appl. .

8706590 1/1987 PCT Int'l Appl. .

OTHER PUBLICATIONS

Dyall-Smith et al. Nuc. Acids Res. 12: 3973-3982 (1984).

Richardson et al. J. Virol. 51: 860-862 (1984).

Holland et al. Science 215: 1577-1585 (1982).

Lin et al. J. Virol. 55 509-512 (1985).

Hoshino et al. J. Infect. Dis. 149: 694-701.

Coulson et al. Virol. 154: 302-312 (1986).

Gerna et al. J. Clin. Micro. 26 1388-1392 (1988).

Coulson et al. (1987) J. Clin. Micro. 25: 509-515.

Young et al. (1983) Proc. Nat'l. Acad. Sci. USA 80: 1194-1198.

Dyall-Smith, M. L., et al. (1981) Gene-coding assignments of rotavirus double-stranded RNA segments 10 and 11. *J. Virol.* 38: 1099-1103.

Kalica, A. R., et al. Genes of human (strain Wa) and bovine (Strain UK) rotaviruses that code for neutralization and subgroup antigens. *Virology* 112: 385-390.

Wyatt, R. G. et al. (1982) Definition of human rotavirus serotypes by plaque reduction assay. *Infect. Immun.* 37: 110-115.

Dyall-Smith, M. L., et al. (1983) Gene mapping of rotavirus double-stranded RNA segments by northern blot hybridication: Application to segments 7,8 and 9. *J. Virol.* 46: 317-320.

Dyall-Smith, et al. (1983) Cloning and sequence of UK bovine rotavirus gene segment 7: marked sequence homology with simian rotavirus gene segment 8. *Nucleic Acids Res.* 11: 3351-3362.

Both, G. W. et al. (1983) Serotype-specific glycoprotein of simian 11 rotavirus: coding assignment and gene sequence. *Proc. Natl. Acad. Sci. USA* 80: 3091-3095.

(List continued on next page.)

*Primary Examiner*—Charles L. Patterson, Jr.

*Assistant Examiner*—G. E. Bugalsky

*Attorney, Agent, or Firm*—Scully, Scott, Murphy & Presser

[57] ABSTRACT

A human rotavirus gene encoding the major outer capsid glycoprotein (VP7) of the human rotavirus serotype 4 or a portion or sub-unit thereof. Expression vectors containing such a gene and expressing all or part of VP7 protein of human rotavirus serotype 4. Polyeptides corresponding to all or part of the VP7 protein of human rotavirus serotype 4 and vaccines containing such polypeptides.

16 Claims, 2 Drawing Sheets

OTHER PUBLICATIONS

Elleman, T. C. et al. (1983) Nucleotide sequence of the gene encoding the serotype-specific glycoprotein of UK bovine rotavirus *Nucleic Acids. Res.* 11: 4689–4701.

Gunn, P. R. et al. (1985) Rotavirus Neutralizing Protein VP7: Antigenic Determinants Investigated by Sequence analysis and Peptide Synthesis. *J. Virol.* 54: 791–797.

Rivier, D. A., et al. (1985) Towards purification of the outer shell polypeptide (VP&) specific for the newly identified human serotype 4 rotavirus. *Experientia* 41: 789.

Dyall-Smith, M. L. (1986) Location of the major antigenic sites involved in rotavirus serotype-specific neutralizations. *Proc. Natl. Acad. Sci. USA* 83: 3465–3468.

McGrae, M. A., et al. (1987) Expression of a major bovine rotavirus neutralization antigen (VP7c) in *Eschericia coli. Gene* 55: 9–18.

ST-3 Segment 9 5'-GGCTTTAAAAGAGAGAATTTCCGTCTGGCTAGCGGATAGCTCCTTTTA 48

```
                                                                                123
ATG TAT GGT ATT GAA TAT ACC ACA GTT CTA  TTT TAT TTG ATA TCG TTC GTT CTT GTG AGT TAT ATT CTG AAA ACC
Met Tyr Gly Ile Glu Tyr Thr Thr Val Leu  Phe Tyr Leu Ile Ser Phe Val Leu Val Leu Tyr Ile Leu Lys Thr
                                                                                25

                                                                                198
ATA ATA AAG ATA ATG GAC TAT ATT ATT TAT AGA ATA GCA TTT GTA ATT GTA GTA TTA TCA GTA TTA TCG AAT GCA
Ile Ile Lys Ile Met Asp Tyr Ile Ile Tyr Arg Ile Ala Phe Val Ile Val Val Leu Ser Val Leu Ser Asn Ala
                                                                                50

                                                              *                 273
CAA AAT TAT GGA ATA AAT TTG CCA ATT ACT GGA TCT ATG GAT ACA GCA TAT GCT AAC TCA ACA CAA GAC AAT AAT
Gln Asn Tyr Gly Ile Asn Leu Pro Ile Thr Gly Ser Met Asp Thr Ala Tyr Ala Asn Ser Thr Gln Asp Asn Asn
                                                                                75

                                                                                348
TTT TTA GTT TCA ACT TTA TGT CTA TAT TAT CCA TCA GAA GCT CCA ACT CAA ATT AGT GAC ACT GAA TGG AAA GAT
Phe Leu Val Ser Thr Leu Cys Leu Tyr Tyr Pro Ser Glu Ala Pro Thr Gln Ile Ser Asp Thr Glu Trp Lys Asp
                                           [---------------A-REGION---------------]  100

                                                                                423
ACA CTA TCT CAG CTG TTT TTA ACC AAA GGA TGG CCG ACA GGT TCA GTT TAT TTT AAT GAA TAT TCA AAC GTT TTA
Thr Leu Ser Gln Leu Phe Leu Thr Lys Gly Try Pro Thr Gly Ser Val Tyr Phe Asn Glu Tyr Ser Asn Val Leu
                                                                                125

                                                                                498
GAA TTT TCC ATC GAC CCA AAG CTA TAC TGT GAT TAT AAT GTT GTG CTA ATT AGA TTC GTT TCT GGT GAG GAG TTG
Glu Phe Ser Ile Asp Pro Lys Leu Tyr Cys Asp Tyr Asn Val Val Leu Ile Arg Phe Val Ser Gly Glu Glu Leu
                                                                 [-------B-REGION-------]  150

                                                                                573
GAC ATA TCT GAA TTA GCT GAT CTA ATA CTG AAT GAG TGG TTA TGT AAT CCA ATG GAT ATA ACA TTA TAT TAT TAC
Asp Ile Ser Glu Leu Ala Asp Leu Ile Leu Asn Glu Trp Leu Cys Asn Pro Met Asp Ile Thr Leu Tyr Tyr Tyr
                                                                                175
```

FIGURE 1a

```
                                                                                                       648
CAA CAA ACT GGA GAG GCA AAC AAA TGG ATA TCA ATG GGA TCA TCA TGT ACC GTT AAA GTG TGT CCA TTA AAT ACT
Gln Gln Thr Gly Glu Ala Asn Lys Trp Ile Ser Met Gly Ser Ser Cys Thr Val Lys Val Cys Pro Leu Asn Thr
                                                                                                       200

                                                                                                       723
CAG ACA TTA GGA ATT GGA TGT CAA ACG ACA AAT ACA GCT ACT TTT GAA ACA GTT GCT GAT AGC GAA AAA TTG GCA
Gln Thr Leu Gly Ile Gly Cys Gln Thr Thr Asn Thr Ala Thr Phe Glu Thr Val Ala Asp Ser Glu Lys Leu Ala
                                        [------------------C-REGION----------------------]            225

                                                *                                                      798
ATA ATT GAT GTT GTC TAC ATC GTA AAT CAT AAA TTA AAT ATC ACA TCT ACT ACA TGT ACA ATA CGG AAT TGT AAT
Ile Ile Asp Val Val Tyr Ile Val Asn His Lys Leu Asn Thr Thr Ser Thr Thr Cys Thr Ile Arg Asn Cys Asn
                                                                                                       250

                                                                                                       873
AAA CTA GGA CCG AGA GAA AAT GTG GCT ATA ATA CAG GTT GGC GGT TCT AAT ATA TTA GAT ATA ACA GCT GAT CCC
Lys Leu Gly Pro Arg Glu Asn Val Ala Ile Ile Gln Val Gly Gly Ser Asn Ile Leu Asp Ile Thr Ala Asp Pro
                                                                                                       275

                                                                                                       948
ACA ACT TCT CCA CAA ACA GAA CGA ATG ATG CGC GTA AAC TGG AAA AAA TGG TGG CAA GTA TTC TAC ACT GTA GTT
Thr Thr Ser Pro Gln Thr Glu Arg Met Met Arg Val Asn Trp Lys Lys Trp Trp Gln Val Phe Tyr Thr Val Val
                                                                                                       300

                                                                                                       1023
GAT TAC ATT AAT CAG ATA GTA CAA GTA ATG TCC AAA AGA TCA AGA TCG TTA GAT TCG TCA GCT TTC TAT TAT AGA
Asp Tyr Ile Asn Gln Ile Val Gln Val Met Ser Lys Arg Ser Arg Ser Leu Asp Ser Ser Ala Phe Tyr Tyr Arg
                                                                                                       325

                                             1062
GTG TAG ATATATCCTAAAATAGAACTGTTTGATGTGACC-3'
Val Term.
  326
```

FIGURE 1b

RECOMBINANT HUMAN ROTAVIRUS VP7 SEROTYPE 4

This is a continuation of copending application Ser. No. 473,959, filed as PCT/AU88/00298, Aug. 10, 1988 now abandoned.

FIELD OF THE INVENTION

The present invention relates to a human rotavirus gene encoding the major outer capsid glycoprotein (VP7) of human rotavirus serotype 4. The invention further relates to sub-units of said gene, protein products thereof, diagnostic reagents and vaccines.

BACKGROUND OF THE INVENTION

Rotaviruses have been shown to be the single most important cause of infantile gastroenteritis (Holmes, I. H., Rotaviruses, in *The Reoviridae* Ed. W. K. Joklik, Plenum: 395-399) and are also important pathogens in many animal species, particularly calves and piglets. In many third world countries rotavirus infection causes significant infant mortality. The World Health Organization has recommended that a vaccine against human rotavirus be developed as soon as possible (Bull. W. H. O. 1983, 61: 251-254).

At present, five serotypes of human rotavirus are known (Hoshino, et al. 1984, J. Infect. Dis. 149: 694-702 and Albert et al., Arch. Virol. 93: 123-130) and it has previously been shown that the virus serotype is determined by the major outer capsid glycoprotein VP7 (also called gp34) (Kalica et al. 1981, Virology 112: 385-390; Dyall-Smith et al. 1983a, J. Virol. 46: 317-320; Kantharidis, et al. 1983, J. Virol. 48: 330-334; Sonza et al., 1983, J. Virol. 45: 1143-1146; Dyall-Smith, et al. 1984, Nucleic Acids Res. 12: 3973-3982). A vaccine effective against rotaviral infection may require representative viruses or VP7 protein antigens of all known serotypes in order to elicit protective immunity against all human serotypes (Gaul, et al. 1982, J. Clin. Micro. 16: 495-503) due to the poor cross reactivity of VP7 protein antigens.

BRIEF DESCRIPTION OF THE DRAWINGS

FIGS. 1*a* and 1*b* show the complete nucleotide sequence of a gene encoding the VP7 protein of human rotavirus serotype 4 and the deduced protein sequence thereof. Nucleotides have been numbered from the 5′ end and amino acids have been numbered from the amino terminal end. Potential glycolsylatoin sites are marked with an asterisk (*) and antigenic sites have been denoted with brackets [].

DETAILED DESCRIPTION OF THE INVENTION

The present invention arises from the isolation and characterization of a human rotavirus VP7 gene corresponding to human rotavirus serotype 4.

According to one aspect of the present invention, there is provided an isolated gene which encodes all or part of the major outer capsid glycoprotein (VP7) of human rotavirus serotype 4.

The gene encoding the serotype 4 VP7 may be in the form of double or single stranded DNA or RNA.

In particular, in this aspect of the invention, there is provided a gene corresponding to or containing the nucleotide sequence set out in FIGS. 1*a* and 1*b* hereof, or a portion or sub-unit of said sequence. The reference to a portion or sub-unit of the nucleotide sequence of FIGS. 1*a* and 1*b* refers to any DNA sequence (or corresponding RNA sequence) within that sequence which encodes a polypeptide capable of eliciting antibodies in a host animal which bind to the VP7 protein of human serotype 4. In particular, this includes one or more of the A(nucleotides 307-336), B(nucleotides 481-498) and C(nucleotides 679-717) regions of FIGS. 1*a* and 1*b*. The A, B and C regions may be ligated to one another to form, for example, an A-B hybrid or B-C hybrid. Such hybrid molecules are included within the scope of the present invention.

The isolated gene encoding all or part of the VP7 protein of human serotype 4 may be inserted into an appropriate expression vector, such as a bacterial plasmid, SV40, adenovirus or phage DNA, for expression of the corresponding polypeptide in host cells (including bacterial or yeast and other eukaryotic host cells) containing these vectors or derivatives thereof.

In accordance with another aspect of the invention, there is provided an expression vector containing a gene encoding all or part of the VP7 protein of human rotavirus serotype 4. Additionally, there are provided host cells containing such a vector.

Depending upon the type of expression vector utilised, the VP7 protein or a sub-unit thereof may accumulate in a host cell, be excreted from the host cell, e.g. into a culture medium, or may accumulate in the outer membrane of the host cell or on the cell surface of the host cell. The use of expression vectors which include appropriate portions of genes encoding outer membrane proteins of prokaryotes, such as *E. coli* or Salmonella, will result in expression of the desired protein product in or at the cell surface. Examples of such vectors are those based on the LamB, TraT, OmpA, phoE or OmpB genes of *E. coli* (Charbit et al. 1986, EMBO 5: 3029-3037; European Patent Application No. 81306190; Charbit et al. 1987, J. Immunol, 139: 1658-1664; Agterberg et al. 1987, Gene 59: 145-150; and Tommassen et al. 1987, FEBS 221: 226-230). Using such vectors, the VP7 protein may be expressed at the cell surface as a fusion protein with an outer-membrane protein.

The polypeptides encoded by the gene, or a portion or sub-unit thereof in accordance with the present invention may form the basis of successful vaccines against rotaviral infections.

In one method of vaccine production, the isolated gene, or a portion or sub-unit thereof, in accordance with the present invention may be inserted into an expression vector, which is then transfected into host bacteria or yeast cells can then be used in large scale production of the corresponding polypeptides. The polypeptides can then be recovered and used as vaccines. Alternatively, and more preferably, the gene, or a portion or sub-unit thereof, in accordance with the present invention may be inserted into an expression vector, and then transfected into a microorganism which subsequently expresses the protein products on, or in association with, the cell surface as previously described. Suitable microorganisms include *E. coli* and Salmonella strains, and in particular, Salmonella strain Ty21A. Suitable microorganisms expressing the major VP7 protein of human rotavirus serotype 4 or portions thereof on the cell surface will, on administration, enter the intestine, invade the lining of the gut, normally through gut-associated lymphold tissue such as the Peyers patches, causing the production of protective antibodies in situ.

Alternatively, a vaccine may comprise the isolated gene, or a portion or sub-unit thereof, in accordance with the present invention, inserted into a vital vector such as adenovirus or vaccinia.

Bacterial or vital vaccines may employ bacteria or viruses dispersed in a pharmaceutical diluent such as a liquid suitable for oral administration. Alternatively the bacteria or viruses may be freeze dried and administered in a solid form.

According to a yet further aspect of the present invention, there is provided a vaccine comprising one or more polypeptides corresponding to all or part of the VP7 protein of human rotavirus serotype 4 or, bacteria having said one or more such polypeptides on or in association with their cell surface, or a vital vector, such as adenovirus, which express said one or more such polypeptides. The vaccine may include one or more adjuvants or pharmaceutically acceptable carriers or excipients.

According to a further aspect of the present invention, there is provided a protein or peptide comprising or containing the peptide sequence of the VP7 protein of human rotavirus serotype 4, or a portion thereof. In particular, in this aspect of the invention, there is provided a polypeptide comprising or containing the peptide sequence set out in FIGS. 1_a_ and 1_b_ or a portion thereof which contains one or more of regions A, B and C of FIGS. 1_a_ and 1_b_.

Polypeptides corresponding to the VP7 protein of human rotavirus serotype 4 or part thereof, may be directly synthesized by known peptide synthetic methods (Atherton et al. 1985, J. Chem. Soc. Commun. 165-166). Alternatively, such polypeptides may be prepared by expression of the gene encoding the VP7 or part thereof in a host cell.

The reference to part of the protein sequence shown in FIGS. 1_a_ and 1_b_ refers to a peptide which is capable of eliciting antibodies in a host animal which bind to the VP7 protein of human rotavirus serotype 4.

The protein sequences corresponding to regions A, B and C of the DNA sequences shown in FIGS. 1_a_ and 1_b_ represent important antigenic regions involved in antibody neutralisation. This has been shown in previous work on the VP7 protein of SAll (monkey) rotaviruses (Dyall-Smith et al. 1986, Proc. Natl. Acad. Sci. (U.S.A.) 83: 3465-3468). Within a serotype, the amino acid sequences corresponding to the regions A, B and C are highly conserved. Between serotypes, these regions are different, and these differences produce the antigenic properties of VP7 which distinguish one serotype from another by cross neutralisation tests. Accordingly, DNA or RNA probes corresponding to the A, B or C regions of FIGS. 1_a_ and 1_b_ or portions thereof, may be used to determine the serotype of a rotavirus isolate or sample. For example, a synthetic oligonucleotide corresponding to the A region of FIG. 1_a_ may be produced by standard chemical Procedures (Rigby et al. 1977, J. Mol. Biol. 113: 237-251), labelled with $^{32}P$ or other isotopic or non-isotopic label, and hybridized with nucleic acids of a rotavirus isolate or sample..If binding is detected, the rotavirus isolate represents serotype 4 as the A region of FIG. 1_a_ is conserved only in this serotype.

According to a further aspect of the present invention there is provided a method for detecting the presence of serotype 4 human rotavirus in a sample which comprises hybridizing nucleic acids of the rotavirus sample with a labelled nucleic acid probe corresponding or complementary to at least one of the A, B or C regions of FIGS. 1_a_ and 1_b_ or a portion of such regions, and detecting whether binding of said nucleic acid probe to nucleic acids in the rotavirus sample has occurred. Such methods may be carried out in solution, or on a solid phase, utilizing standard conditions of hybridization (Anderson et al. 1985, Quantitative Filter Hybridization in *Nucleic Acid Hybridization; A Practical Approach,* Hames, eds. IRL Press Oxford, p. 91-111).

According to a still further aspect of the present invention, there is provided a kit for detecting human rotavirus of the type 4 serotype comprising one or more nucleic acid probes corresponding to the A, B or C regions of FIGS. 1_a_ and 1_b_ or portions thereof, which may be labelled with a detectable marker, together with appropriate buffers and/or solutions for carrying out assays for detecting binding of said nucleic acids to rotavirus nucleic acids.

The gene encoding human rotavirus serotype 4 or a portion or sub-unit thereof, is not restricted to the specific DNA sequences shown in FIGS. 1_a_ and 1_b_ or the equivalent RNA sequence, but rather includes variants of such a sequence where nucleotides have been substituted, added to or deleted from the sequence shown in FIGS. 1_a_ and 1_b_ with the proviso that these variants encode proteins having substantially the same antigenicity and host protective ability as the major outer capsid glycoprotein of serotype 4, or portions thereof. Similarly, the polypeptide sequence shown in FIGS. 1_a_ and 1_b_ may have amino acids added, substituted or deleted with the same proviso as above.

The term "polypeptide" used herein includes a polypeptide bearing one or more carbohydrate moieties.

The invention will now be further illustrated with reference to the following non-limiting Examples and FIGS. 1_a_ and 1_b_.

EXAMPLE 1

Materials and Methods

Human Rotavirus ST3 was obtained from Dr. T. H. Flewett, East Birmingham Hospital, U.K. This rotavirus strain was first isolated in the United Kingdom in 1975, and is widely available.

DNA Sequencing

Sequences were determined from the M13 ss DNA template according to the Sanger Chain termination method (Sanger et al. 1977, Proc. Natl. Acad. Sci. U.S.A. 74: 5463-5467).

RNA sequencing was carried out according to the method of Karanthanasis (Karanthanasis, P. 1982 Focus 4:6-7). Briefly, an oligonucleotide primer having the sequence 5'GCTTCIGITGGATAATA3' (corresponding to nucleotides 300-315 of clone ST3 16) was annealed to RNA (1-10 mg) isolated from human rotavirus ST3 (according to methods described hereinafter). The sequence of the RNA was then determined according to the Sanger Chain termination method (Sanger et al.).

Identification of cDNA encoding human Serotype 4 VP7

The ST3 virus was grown in cell culture, purified and RNA extracted as described previously (Dyall-Smith et al. 1984 and Wyatt et al. 1983, J. Clin. Micro. 18: 310-317). Briefly, virus particles were treated with 10 ug/ml trypsin at room temperature for 15 minutes and innoculated with MA104 cells (Dyall-Smith et al. 1981, J. Virol. 38: 1099–1103) which were washed to remove fetal calf serum (FCS). Virus was allowed to absorb for 1 hour at 37° C. After incubation for 3 days in the presence of gentamycin, the cells were disrupted with Arklone (ICI chemicals) and viruses particles separated by centrifugation (75 min at 27G). The virus particles were then layered onto a 60%–30% glycerol gradient and centrifuged for 1–2 hours at 25K. Virus particles were harvested from the gradient, and sedimented by centrifugation in a solution of Tris-HCl/saline/calcium (50 mm Tris pH 7.4, 2 mm $CaCl_2$, 0.15 m NaCl). The virus pellet was resuspended in Tris-HCl/saline/calcium and 50% glycerol.

The virus particles were extracted with phenol/-chloroform (1:1) and RNA was precipitated with NaAcetate:ethanol (1:2.5) according to the methods of Maniatis et al. (*Molecular Cloning: A Laboratory Manual,* 1982, Cold Spring Harbor).

RNA was recovered by precipitation and resuspended in stock solution A (100 mMTris HCl pH 8.0; 20 mM MgAcetate; 50 mM NaCl; 1 mg/m/BSA; 2 mM DTT and 5 mM $MnCl_2$). The RNA solution was denatured at 100° C.; for 5 minutes, snap chilled on ice, and then incubated with polynucleotide transferase (1–2 units) and 10 mM ribose ATP (rATP) for 1 hour at 37° C. to poly A tail the RNA. The reaction was terminated with EDTA, extracted with phenol/chloroform and precipitated with NaAcetate/ethanol. The precipitate was recovered by centrifugation prior to cDNA synthesis;

cDNA Synthesis

The poly A tailed RNA was heat denatured (100° C., 5 min) and reversed transcribed in the presence of oligo-dT according to Maniatis et al. The RNA template was hydrolysed in the presence of EDTA (65° C. for 30 min) and NaOH (130 mM.). The mixture was neutralised with 1M Tris-HCl pH 8.0, extracted with phenol/-chloroform and chromatographed on sephadex G-50 (Pharmacia, Uppsala Sweden) to remove free deoxynucleotide triphosphates (dNTP's). The resultant single stranded DNA was recovered by precipitation, resuspended in annealing buffer (0.15M NaCl) and then incubated under annealing conditions (100° C. for 2 min, 70° C. for 20 min, then 57° C. for 1 hour). The annealed double-stranded DNA was precipitated, resuspended in DDW (deionized distilled water) and end repaired with T4 DNA polymerase according to Maniatis et al. The DNA was recovered by centrifugation, resuspended in DDW and fractionated by electrophoresis in a 1% agarose gel. DNA having a molecular weight of 1.1 Kb (corresponding to VP7-Dyall-Smith et al. 1983a was recovered according to the procedure of Maniatis et al. Homopolymeric tails of dC (deoxycytidine) were then added using terminal transferase Maniatis et al.). The C-tailed DNA was then annealed to dG-tailed pBR 322 (Maniatis et al.).

*E-coli* MC 106 (Casadaban, et al. 1980, J. Mol. Biol. 138: 179–207) was then transformed with the ds cDNA-pBR322 preparation and transformants containing hybrid plasmids were selected by screening for resistance to tetracycline and sensitivity to ampicillin (Maniatis et al.).

Identification of VP7 Containing Colonies

Colonies were streaked onto a nylon membrane (Nylon-N, Amersham) and incubated on an agar plate containing tetracycline, 15 ug/ml, and incubated at 37° C. overnight. Colonies were lysed with 1.5M NaCl/0.5M NaOH and then neutralised with 1.5M NaCl/0.5M Tris-HCl, pH 7.2, 0.1M EDTA. Membranes were washed with 2XSSC (Maniatis et al.) and fixed onto the membrane using a U.V. light source. The membrane was prehybridized according to standard procedures (Maniatis et al.) and then hybridised with segment 9 of Wa ds RNA prepared by the method described in Dyall-Smith et al. 1983b, Nucleic Acids Res. 11: 3351–3362 at page 3354 labelled with $^{32}P$ according to the methods of Maniatis et al. Colonies which hybridised with the labelled probe (as detected by autoradiography) were isolated, grown up in L-Broth and plasmid DNA recovered according to standard procedures (Maniatis et al.). Clones which hybridised with the probe were analysed for insert size by agarose gel electrophoresis, and inserts were recovered following incubation with Pstl and electrophoresis on a 1% agarose gel. Two clones, ST3 16 and ST3 65 were selected for further characterisation. The nucleotide sequence of the VP7 insert of these clones was determined by the method of Sanger et al.

By reference to known human VP7 sequences (Dyall-Smith et al. 1984), clone ST3 16 was shown to begin at nucleotide 136 and end at nucleotide 652. Clone ST3 65 starts at nucleotide 394 and ends at nucleotide 1062.

The sequence of clones ST3 16 and ST3 65 share a common sequence of 258 nucleotides, that is, nucleotides 394 to 652 of the serotype 4 VP7 sequence. This common sequence contains a unique Sspl site at nucleotide 407, which was used to construct a cDNA clone which extended from nucleotides 136 to 1062 of the VP7 sequence. The combined clone, hereafter referred to as ST3 90, was prepared by firstly cleaving ST3 16 with Sspl. Clone ST3 65 was also cleaved with Sspl, and the C-terminal fragment from one Sspl digestion was isolated by electrophoresis. The C-terminal fragment from ST3 65 was then ligated to the Sspl fragment from ST3 16 to form ST3 90 which as set out above extends from nucleotides 136 to 1062. The nucleotide and deduced protein Sequence of clone ST3 90 insert is set out in FIGS. 1*a* and 1*b* at nucleotides 136 to 1062. The 5′ untranslated sequence and the sequence of nucleotides 1 through 136 were determined by RNA sequencing (Karanthanasis). The deduced protein sequence of the human rotavirus type 4 serotype is also shown. Potential glycosylation sites are shown with an asterix. The VP7 of serotype 4 is shown by FIGS. 1*a* and 1*b* to consist of 326 amino acids.

Important antigenic regions A, B and C (FIGS. 1*a* and 1*b*) have been deduced from their nucleotide sequence, and by comparison with the VP7 genes of other human serotypes (Dyall-Smith et al. 1986 and Both et al. 1983, Proc. Natl. Acad. Sci. U.S.A. 80: 3091–3095). The A region corresponds to nucleotides 307–336; the B region corresponds to nucleotides 481–498; and the C region corresponds to nucleotides 679–717 of the gene sequence of FIGS. 1*a* and 1*b*. Each of these regions are underlined in FIGS. 1*a* and 1*b*.

The VP7 gene of the ST3 virus corresponding to the human type 4 serotype shares significant homology with previously published VP7 sequences (Dyall-Smith et al. 1984 and Richardson et al. 1984, J. Virol. 51: 860–862), but differs significantly in the nucleotide and protein sequences of antigenic regions A, B and C. cDNA clone ST3 90 was cloned into the plasmid vector pBR322. For expression of the VP7 protein, the ST3 90 cDNA may be inserted into an appropriate expression vector according to standard procedures (Maniatis et al.).

We can combine the VP7 gene of ST3 with other genes such as the lacZ gene of *E. coli* or outer membrane protein genes from *E. coli* to give a chimetic gene which will give rise to a fusion protein which is part rotavirus protein and part bacterial protein. We can for example use plasmid pPR930, which contains a functional lacZ gene with sites at its 5′ end suitable for inserting coding regions of genes such as the VP7 gene of the ST3 virus. The plasmid pPR930 contains the Bam Hl to Sall, LacZ containing fragment of pMC1403, ligated between the BamHl and Sall sites of pUC18 to give a plasmid in which the lacZ gene is expressed from the lac promoter of pUC18, and the EcoRl, Sstl, Kpnl, Smal, BamHl part of the pUC18 polylinker lies within the 5′ end of the functional lacZ gene.

EXAMPLE 2

Expression of the VP7 Protein of Human Serotype 4

(i) cDNA clone ST3 90 was digested with Pstl and the VP7 fragment corresponding to nucleotides 136–1062 was isolated by agarose gel electrophoresis (Maniatis et al.). This fragment was digested with Ndel (Ndel site between nucleotides 245 and 259) and end-filled with the Klenow fragment of DNA polymerase 1. 8 met EcoR1 linkers were ligated on to this fragment which was then cleaved with EcoR1. This 810 bp fragment was ligated into the plasmid vector pUC18 (Yanische-Perron et al. 1985, Gene 33: 103–119) which had been digested with EcoRl and PstI. The ligation mix was then transformed into *E. coli* strain JM101 (Yanische-Perron et al.) made competent by the method of Dagert and Ehrlich (Pagert et al. 1979, Gene *6: 23–28*).

The resulting clones are in the correct reading frame at the N-terminal end, but out of frame at the C-terminal end. Clones were selected on IPTG/X-gal Miller, J. H. 1972, Experiments in Molecular Genetics, Cold Spring Harbor Laboratory, Cold Spring Harbor IPTG at 20 mg/ml; X-gal at 25 mg/ml) agar plates. White colonies, that is, colonies which contain a DNA insert, were selected. Selected clones were cut with Pst 1 and then treated with Bal 31 nuclease (Boehringer, 3 units, 20 seconds; buffer: 12 mM $CaCl_2$, 2 mM, $MgCl_2$, 200 mM NaCl, 20 mM Tris-HCl (pH 8.0), 1 mM EDNA) to remove nucleotides from the C-terminal end of the ST3 90 insert. The C-terminal end was end repaired with the Klenow fragment of DNA polymerase 1 to give a flush end. The DNA was then digested with ECoRl and the ST3 90 insert recovered by agarose gel electrophoresis. The insert was then ligated into the plasmid vector pPR 930 (Casadaban et al., Methods Enzymol. 100: 293–308) which had been digested with EcoRl/Smal. The resultant clones have a 1 in 3 chance of being in-frame at the C-terminal. In one experiment 60 clones were obtained. These clones were then checked for expression of the serotype4 VP7 or part thereof using an immuno-colony blot and Western blot (Kemp et al. 1981, Proc. Natl. Acad. Sci. 78: 4520–4524). In these techniques, colonies are lysed with a lysis agent, and the liberated proteins fixed onto a support matrix such as nitrocellulose. The support matrix is then probed with a rabbit antiserum against ST3 rotavirus containing antibodies directed against human rotavirus VP7, and antibody binding subsequently detected. Plasmid DNA is prepared from those colonies which react with the anti-VP7 antisera. The inserts encoding the serotype 4 VP7 are then recovered by digestion with EcoR1 and Bam H1, for ligation into other expression vectors.

(ii) Clone ST3 90 was cut with Pstl and the ST3 90 insert was recovered by gel electrophoresis, cut with Nde 1, end filled with the Klenow fragment of DNA polymerase I. This fragment was ligatedinto SmaI cut pUC18 (an expression plasmid Yanische-Perron et al.) and transformed into *E. coli* strain JM101 (Yanische-Perron et al.) Clones containing the ST3 90 insert were selected as white colonies on IPTG/X-gal agar plates. The inserts were in the correct reading frame at the N-terminal end and out of frame at the C-terminus. A selected clone was then digested with BamHI, end filled with the Klenow fragment of DNA polymerase I, cut with Eco Rl, and the resulting fragment ligated into the plasmid pPR 631, which had been digested with EcoRI/SmaI. The recombinant pPR 930 plasmid was then transformed into JM101.

The resultant clones contain VP7 inserts which are inframe at both the C and N-terminal ends. Clones which contained the ST3 90 insert were detected as white colonies on an IPTG/X-gal agar plate. These clones were then tested for the expression of VP7 by reaction with antisera directed against the VP7 of human serotype 4. The insert, which is now in frame at both the N and C-terminal ends of the VP7, is isolated by digestion with EcoRI/BamHI. This fragment is then ready for cloning into. a vector, such as the Lam B expression vector (Charbit et al.), which will express the VP7 on or in association with the cell surface of a microorganism such as Salmonella.

In Examples 1 and 2, all methods; ligation conditions, restriction enzyme conditions, and enzyme reactions are according to Maniatis et al.

We claim:

1. An isolated gene encoding a VP7 protein of human rotavirus serotype 4.

2. The gene according to claim 1 which is double stranded RNA or DNA.

3. The gene according to claim 2 having the nucleotide sequence of FIGS. 1*a* and 1*b*.

4. The gene according to claim 1 which is single stranded RNA and DNA.

5. The gene according to claim 4 having a nucleotide sequence of FIGS. 1*a* and 1*b*.

6. A fragment of an isolated gene encoding a portion of a VP7 polypeptide of human serotype 4, wherein said fragment selectively hybridizes with serotype 4 human rotaviral nucleic acids and detecting a hybridization product so formed.

7. The gene of claim 6 wherein said portion corresponds to the whole of at least one of the A, B or C regions of FIGS. 1*a* and 1*b*.

8. An expression vector which comprises a gene according to claims 1 or 3 or a gene fragment according to claims 7 or 6.

9. The expression vector according to claim 8 which comprises plasmid or phage DNA.

10. A host cell comprising the expression vector according to claim 8.

11. A host cell comprising the expression vector according to claim 9.

12. The host cell according to claim 11 wherein said cell is prokaryotic and wherein the VP7 protein or the portion thereof is expressed on the cell surface.

13. The host cell according to claim 10 wherein said cell is prokaryotic and wherein the VP7 polypeptide or the portion thereof is expressed on the cell surface.

14. An antigenic preparation comprising the host cell of claim 13.

15. A method for detecting the presence of serotype 4 human rotavirus in a sample which comprises hybridizing nucleic acids present in the sample with a labelled VP7 DNA or RNA probe which selectively hybridizes with serotype 4 human rotaviral nucleic acids and detecting a hydridization product so formed.

16. The method of claim 15 wherein said labeled VP7 DNA or RNA probe comprises a nucleic acid corresponding to at least the A, B or C region of FIGS. 1*a* and 1*b* or a portion thereof sufficient to identify serotype 4 rotavirus RNA or DNA.

* * * * *

UNITED STATES PATENT AND TRADEMARK OFFICE

CERTIFICATE OF CORRECTION

PATENT NO. : 5,332,658

DATED : July 26, 1994

INVENTOR(S) : M. L. Dyall-Smith, et al..

It is certified that error appears in the above-indentified patent and that said Letters Patent is hereby corrected as shown below:

On the title page, item [73] Assignee: Delete "Australia", and insert --University of Sydner, New South Wales, both of Australia--.

In the Abstract, line 1: delete "A" and insert --The present invention provides a--
In the Abstract, line 3: delete "Expression" and insert --Also provided are expression--
In the Absttract, line 5: after "Polypeptides" insert --are also provided--
Column 1, line 49: "glycolsylatoin" should read --glycosylation--
Column 2, line 66: "lymphold" should read --lymphoid--
Column 3, lines 3, 5 & 15: "vital" should read --viral--
Column 3, line 60: "sample" should read --sample.--
Column 5, line 53: "1983a" should read --1983a)--
Column 6, line 43: "Sequence" should read --sequence--
Column 7, line 29: "met" should read --mer--
Column 7, line 36: "Pagert" should read --Dagert--
Column 7, line 39: "Miller" should read --((Miller--
Column 7, line 47: "EDNA" should read --EDTA--
Column 7, line 59: "serotype4" should read --serotype 4--
Column 8, line 7: "ligatedinto" should read --ligated into--

Signed and Sealed this

Ninth Day of September, 1997

*Attest:*

Bruce Lehman

BRUCE LEHMAN

*Attesting Officer* *Commissioner of Patents and Trademarks*

UNITED STATES PATENT AND TRADEMARK OFFICE

CERTIFICATE OF CORRECTION

PATENT NO. : 5,332,658

DATED : July 26, 1994

INVENTOR(S) : M. L. Dyall-Smith, et al..

It is certified that error appears in the above-indentified patent and that said Letters Patent is hereby corrected as shown below:

On the title page, item [73] Assignee: Delete "Australia", and insert --University of Sydney, New South Wales, both of Australia--.

In the Abstract, line 1: delete "A" and insert –The present invention provides a–
In the Abstract, line 3: delete "Expression" and insert –– Also provided are expression ––
In the Absttract, line 5: after "Polypeptides" insert –are also provided–
Column 1, line 49: "glycolsylatoin" should read –glycosylation–
Column 2, line 66: "lymphold" should read –lymphoid–
Column 3, lines 3, 5 & 15: "vital" should read –viral–
Column 3, line 60: "sample" should read –sample.–
Column 5, line 53: "1983a" should read –1983a)–
Column 6, line 43: "Sequence" should read –sequence–
Column 7, line 29: "met" should read –mer–
Column 7, line 36: "Pagert" should read –Dagert–
Column 7, line 39: "Miller" should read –((Miller–
Column 7, line 47: "EDNA" should read –EDTA–
Column 7, line 59: "serotype4" should read –serotype 4–

UNITED STATES PATENT AND TRADEMARK OFFICE

CERTIFICATE OF CORRECTION

PATENT NO. : 5,332,658

DATED : July 26, 1994

INVENTOR(S) : M. L. Dyall-Smith, et al.

It is certified that error appears in the above-indentified patent and that said Letters Patent is hereby corrected as shown below:

Column 8, line 7: "ligatedinto" should read -- ligated into --.

This certificate supersedes Certificate of Correction issued September 9, 1997.

Signed and Sealed this

Twenty-first Day of July, 1998

Attest:

BRUCE LEHMAN

Attesting Officer

*Commissioner of Patents and Trademarks*